US00PP14597P29

(12) United States Plant Patent
Jensen

(10) Patent No.: US PP14,597 P2
(45) Date of Patent: Mar. 16, 2004

(54) CAMPANULA PLANT NAMED '10.00.14'

(50) Latin Name: *Campanula×haylodgensis*
Varietal Denomination: 10.00.14

(75) Inventor: Gert K. Jensen, Odense N (DK)

(73) Assignee: Gartneriet PKM ApS, Odense (DK)

( * ) Notice: Subject to any disclaimer, the term of this patent is extended or adjusted under 35 U.S.C. 154(b) by 0 days.

(21) Appl. No.: 10/396,532

(22) Filed: Mar. 25, 2003

(51) Int. Cl.[7] ..... A01H 5/00
(52) U.S. Cl. ..... Plt./263
(58) Field of Search ..... Plt./263

*Primary Examiner*—Kent Bell
(74) *Attorney, Agent, or Firm*—C. A. Whealy

(57) ABSTRACT

A distinct cultivar of Campanula plant named '10.00.14', characterized by its upright and outwardly spreading growth habit; large violet blue campanulate flowers with good longevity; and temperature tolerance from −15 to 35° C.

1 Drawing Sheet

Botanical classification/cultivar designation: *Campanula×haylodgensis* cultivar 10.00.14.

BACKGROUND OF THE INVENTION

The present Invention relates to a new and distinct cultivar of Campanula plant, botanically known as *Campanula× haylodgensis*, and hereinafter referred to by the name '10.00.14'.

The new Campanula is a naturally-occurring branch mutation of an unidentified selection of *Campanula× haylodgensis*, not patented. The cultivar 10.00.14 was discovered and selected by the Inventor from within a population of plants of the unidentified selection of *Campanula× haylodgensis* in a controlled environment in May, 1999, in Odense, Denmark.

Asexual reproduction of the new cultivar by cuttings taken at Odense, Denmark, since June, 2000, has shown that the unique features of this new Campanula are stable and reproduced true to type in successive generations.

SUMMARY OF THE INVENTION

Plants of the cultivar 10.00.14 have not been observed under all possible environmental conditions. The phenotype may vary somewhat with variations in environment such as temperature and/or light intensity without, however, any variance in genotype.

The following traits have been repeatedly observed and are determined to be the unique characteristics of '10.00.14'. These characteristics in combination distinguish '10.00.14' as a new and distinct cultivar:

1. Upright and outwardly spreading growth habit.
2. Large violet blue campanulate flowers with good longevity.
3. Temperature tolerant from −15 to 35° C.

Plants of the new Campanula are most similar to plants of the parent, the unidentified selection of *Campanula× haylodgensis*. Plants of the new Campanula differ from plants of the parent selection in the following characteristics:

1. Plants of the new Campanula are not as freely branching as plants of the parent selection.
2. Plants of the new Campanula are more upright than plants of the parent selection.

3. Plants of the new Campanula have larger leaves and flowers than plants of the parent selection.
4. Flowers of plants of the new Campanula last about 10 days longer than flowers of plants of the parent selection.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ from the color values cited in the detailed botanical description which accurately describe the colors of the new Campanula.

The photograph comprises a close-up view of a typical flowering stem of the unidentified selection of *Campanula× haylodgensis* (left) and '10.00.14' (right).

DETAILED BOTANICAL DESCRIPTION

In the following description, color references are made to The Royal Horticultural Society Colour Chart, 2001 Edition, except where general terms of ordinary dictionary significance are used. Plants used for the above-mentioned photographs and botanical description were grown in Odense, Denmark in 10.5-cm containers in a glass-covered greenhouse. During the production of the plants, day temperatures were about 17° C., night temperatures were about 21° C., and light levels were about 25 W/m$^2$. Plants used were about 22 weeks old when the photographs and description were taken.

Botanical classification: *Campanula×haylodgensis* cultivar 10.00.14.

Parentage: Naturally-occurring branch mutation of an unidentified selection of *Campanula×haylodgensis*, not patented.

Propagation:

*Type.*—*By* cuttings.

*Time to initiate roots.*—About 16 to 18 days at 16 to 18° C.

*Root description.*—Fibrous, fine; white in color.

Plant description:

*Form.*—Upright and outwardly spreading; rounded inverted triangle.

*Plant height, soil level to top of plant plane.*—About 20 cm.

*Plant width.*—About 20 cm.

*Lateral branch description.*—Quantity: About 20 to 25 per plant. Length: About 30 cm. Texture: Smooth, glabrous. Color: 144A to 137A.

*Foliage description.*—Arrangement: Alternate, simple. Quantity per lateral branch: About 8 to 10. Length: About 1.8 cm. Width: About 7 mm. Shape: Ovate. Apex: Acute. Base: Acute. Margin: Serrate. Texture, upper and lower surfaces: Smooth, glabrous. Venation pattern: Pinnate. Color: Developing foliage, upper surface: 144B. Developing foliage, lower surface: 144C. Fully expanded foliage, upper and lower surfaces: 136A. Venation, upper and lower surfaces: 144A. Petiole: Length: About 3 to 7 mm. Diameter: About 1 mm. Texture, upper and lower surfaces: Smooth; glabrous. Color, upper surface: 136A. Color, lower surface: 138A.

Flower description:

*Flower type and habit.*—Large multi-petalled campanulate flowers arranged in terminal panicles. Flowers face upright and outward. Flowers persistent.

Fragrance.—Very faint.

*Natural flowering season.*—Continuously flowering during July in northern Europe.

*Quantity.*—Freely flowering with about three to four flowers per lateral branch.

*Flower longevity on the plant.*—About 60 days.

*Flower diameter.*—About 2.4 cm.

*Flower depth (height).*—About 1.5 cm.

*Flower buds.*—Length: About 7 mm. Diameter: About 6 mm. Shape: Ovate. Color: 92B.

*Petals.*—Quantity per flower: About 20 to 25. Length: About 1.2 to 1.4 cm. Width: About 9 to 12 mm. Shape: Ovate. Apex: Acuminate. Margin: Entire. Texture, upper and lower surfaces: Smooth; glabrous; satiny. Color: Upper surface, when opening and fully opened: 92B; color becoming closer to 92C to 92D with development. Lower surface, when opening and fully opened: 92A to 92B.

*Sepals.*—Quantity per flower: About eight. Length: About 4 mm. Diameter: About 1.5 mm. Shape: Lanceolate. Apex: Acute. Margin: Entire. Color, upper and lower surfaces: Close to 136A.

*Reproductive organs.*—Androecium: Stamens and pistils deformed. Stamens per flower: About five. Anther shape: Linear. Anther length: About 2 mm. Anther color: 16A. Pollen amount: None. Gynoecium: Quantity of pistils per flower: One. Style length: About 1.2 cm. Style color: 138B.

*Seeds/fruit.*—Seed and fruit production have not been observed.

Disease/pest resistance: Under commercial production conditions, plants of the new Campanula have not been noted to be resistant to pathogens or pests common to Campanula.

Temperature tolerance: Plants of the new Campanula have been observed to tolerate temperatures from −15 to 35° C. in Odense, Denmark.

It is claimed:

1. A new and distinct cultivar of Campanula plant named '10.00.14', as illustrated and described.

* * * * *

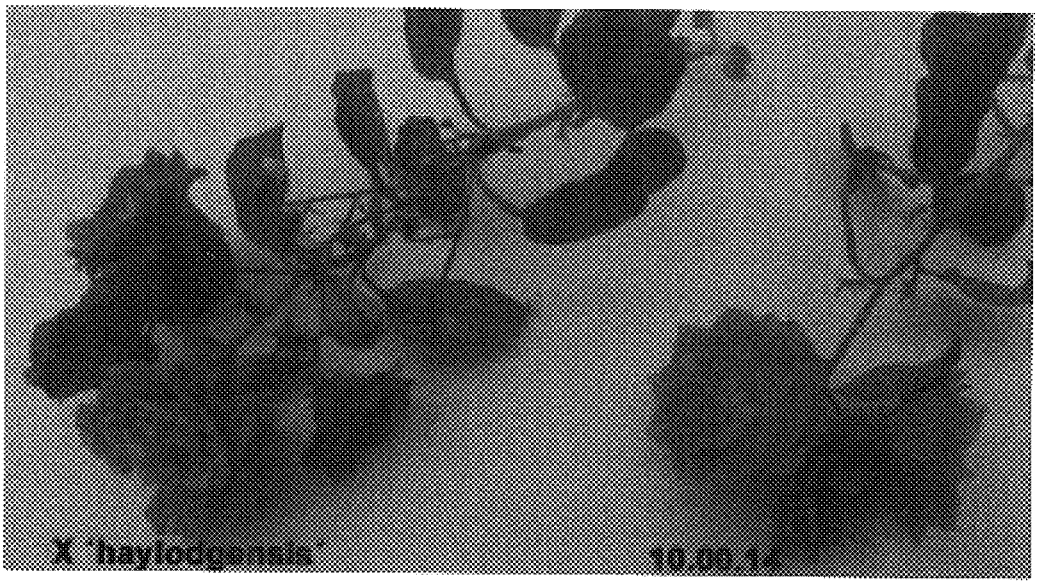
X 'haylodgensis'
10.08.14